(12) United States Patent
Zhang et al.

(10) Patent No.: US 8,679,850 B2
(45) Date of Patent: Mar. 25, 2014

(54) METHODS OF CATIONIC POLYMER DETECTION

(75) Inventors: Guixi Zhang, Shanghai (CN); Sijing Wang, Shanghai (CN); Hong Xu, Shanghai (CN); Xiaofeng Tang, Shanghai (CN)

(73) Assignee: General Electric Company, Schenectady, NY (US)

( * ) Notice: Subject to any disclaimer, the term of this patent is extended or adjusted under 35 U.S.C. 154(b) by 231 days.

(21) Appl. No.: 13/119,295

(22) PCT Filed: Dec. 21, 2010

(86) PCT No.: PCT/CN2010/002112
§ 371 (c)(1),
(2), (4) Date: Mar. 16, 2011

(87) PCT Pub. No.: WO2012/083492
PCT Pub. Date: Jun. 28, 2012

(65) Prior Publication Data
US 2012/0270328 A1    Oct. 25, 2012

(51) Int. Cl.
*G01N 21/49* (2006.01)
(52) U.S. Cl.
USPC .............................. 436/85; 436/164; 210/745
(58) Field of Classification Search
USPC ...................................... 436/85, 164; 210/745
See application file for complete search history.

(56) References Cited

U.S. PATENT DOCUMENTS

| 4,813,973 | A | 3/1989 | Winnik et al. |
| 4,869,845 | A | 9/1989 | Chen |
| 5,171,450 | A | 12/1992 | Hoots |
| 5,593,850 | A | 1/1997 | Wetegrove et al. |
| 5,705,394 | A | 1/1998 | Ananthasubramanian et al. |
| 6,077,461 | A | 6/2000 | Murray et al. |
| 6,153,110 | A * | 11/2000 | Richardson et al. .......... 210/739 |
| 6,197,522 | B1 | 3/2001 | Keller et al. |
| 6,238,486 | B1 | 5/2001 | Dunham et al. |

(Continued)

FOREIGN PATENT DOCUMENTS

WO    WO2008147618    *    4/2008

OTHER PUBLICATIONS

The Influence of Water Clarification Chemicals on Deposit Control Polymer Performance in Cooling Water Applications Zahid Amjad, Robert Zuhl Association of Water Technologies Inc. 2002 Annual Convention and Exposition. Sep. 18-22, 2002.*

The Influence of Water System Impurities on the Performance of Deposit Control Polymers as Particulate Dispersants Zahid Amjad, Robert Zuhl Association of Water Technologies Inc. 2001 Annual Convention. Oct. 9-13, 2001.*

(Continued)

*Primary Examiner* — Krishnan S Menon
*Assistant Examiner* — Dwan A Gerido
(74) *Attorney, Agent, or Firm* — Wegman, Hessler & Vanderburg (57) ABSTRACT

The present invention concerns a method of detecting cationic polymers comprising: obtaining a target water sample containing a cationic polymer; adding a polymer dispersant solution and a phosphate solution to the target water sample, the polymer dispersant solution is comprised of a polymer dispersant with calcium and magnesium hardness and the phosphate solution is comprised of a phosphate; standing the target water sample; and measuring the turbidity of the target water sample; comparing the turbidity of said target water sample with a calibration curve of the turbidity of samples containing known concentrations of cationic polymers to determine the concentration of cationic polymers in said target water sample.

22 Claims, 4 Drawing Sheets

(56) References Cited

U.S. PATENT DOCUMENTS

| | | |
|---|---|---|
| 6,312,644 B1 | 11/2001 | Moriarty et al. |
| 6,420,530 B1 | 7/2002 | Weatherby et al. |
| 6,441,754 B1 | 8/2002 | Wang et al. |
| 6,444,747 B1 | 9/2002 | Chen et al. |
| 6,911,534 B2 | 6/2005 | Weatherby et al. |
| 8,178,353 B2 * | 5/2012 | Xiao et al. .................. 436/85 |
| 2008/0223790 A1 * | 9/2008 | Blandford et al. ............ 210/700 |
| 2008/0295581 A1 | 12/2008 | Zhang et al. |

OTHER PUBLICATIONS

Becker et al., Detection of Polyelectrolytes at Trace Levels in Water by Fluorescent tagging. Reactive and Function Polymers 60(2004) 183-193.

* cited by examiner

METHODS OF CATIONIC POLYMER DETECTION

BACKGROUND OF THE INVENTION

1. Field of the Invention

This invention is related to the composition and method for detection of cationic polymers in aqueous systems.

2. Description of Related Art

Cationic polymers are widely used in industrial aqueous systems and wastewater treatment process, drinking water treatment process, such as polydiallyldimethylammonium chloride (polyDADMAC), cationic acrylamide copolymers, epichlorohydrin-dimethylamine polymers, and polyethyleneimine. However, the residual cationic polymer is always a concern in some aqueous systems, such as waste water treatment process, drinking water treatment process, food process, membrane treatment process and so on. At the same time, regulations become more rigorous regarding the presence of residual cationic polymers in treated water. Therefore the ability to track the residual polymer concentration in aqueous system is highly desirable to increase in efficiency of the chemical treatment program, allow for diagnostic troubleshooting, and insure to meet regulatory control of residual polymer discharge.

Currently, there are several common types of water-soluble polymer detection methods: (1) settling rate of clay suspensions; (2) size-exclusion chromatograph with ultraviolet detection; (3) turbidmetry of complexes between oppositely charged polymers; (4) fluorescent tagging; (5) colorimetry; and (6) immunoassay method.

Immunoassay techniques are used to determine the presence or concentration of a water treatment polymer in an aqueous system as described in U.S. Pat. No. 6,911,534B2; U.S. Pat. No. 6,420,530; U.S. Pat. No. 6,197,522B1; and U.S. Pat. No. 5,593,850. Monoclonal or polyclonal antibodies to different water treatment polymers are prepared and the antibody is applied as a reagent in an immunoassay on the target aqueous samples. It was reported that immunoassay detection technology was already in existence for coagulant polymers epichlorohydrin-dimethylamine and polydiallyldiammonium chloride and cationic copolymer or terpolymer, which contained monomer of diallyldimethylammonium chloride.

Another approach to detect the polymers is fluorescent tagging techniques, wherein a fluorescent group is introduced to the target polymer molecular structure, either during or after the polymerization, and then utilized for fluorescence monitoring as described in U.S. Pat. Nos. 4,813,973; 5,171,450; 5,705,394; and 6,312,644. With this approach the polymer is positively indicated by florescence. But many aqueous systems wherein the polymers are utilized often contain other sources of fluorescence, therefore, application of fluorescent marker may be impractical, as it becomes difficult to reliably distinguish low levels of fluorescence arising from aqueous systems. Furthermore luminol derived monomer was developed as described in U.S. Pat. No. 6,077,461. The chemiluminescent groups were also introduced to polymer molecule, the chemiluminescent group could be detected with a very low level limit, even in systems containing impurities which either quench fluorescence or fluoresce themselves.

However, the above detection methods generally either have poor sensitivities, which require a preconcentration step, or require the introduction of other functional groups before the polymer structure can be tested. Additionally, these methods often introduce secondary contamination into the tested solution, such as fluorescent groups or non-environmentally friendly dyes, which require extra waste treatment before disposal. Also, these methods require the use of expensive fluorescent monomer, dye and antibodies.

Thus, there exists a strong need for a simplified test method that can easily be used to determine the concentration of cationic polymers in aqueous systems.

SUMMARY OF THE INVENTION

The present invention concerns a method of detecting cationic polymers comprising: obtaining a target water sample containing a cationic polymer; adding a polymer dispersant solution and a phosphate solution to the target water sample, the polymer dispersant solution is comprised of a polymer dispersant with hardness of calcium and magnesium and the phosphate solution is comprised of a phosphate and bicarbonate or carbonate; standing the target water sample; and measuring the turbidity of the target water sample; comparing the turbidity of said target water sample with a calibration curve of the turbidity of samples containing known concentrations of cationic polymers to determine the concentration of cationic polymers in said target water sample.

The present invention and its advantages over the prior art will become apparent upon reading the following detailed description and the appended claims with reference to the accompanying drawings.

BRIEF DESCRIPTION OF THE DRAWINGS

These and other aspects of the invention will be understood from the description and claims herein, taken together with the drawings showing details of construction and illustrative embodiments, wherein:

DETAILED DESCRIPTION OF THE INVENTION

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges stated herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

As used herein, the terms "comprises", "comprising", "includes", "including", "has", "having", or any other variation thereof, are intended to cover a non-exclusive inclusion. For example, a process, method, article or apparatus that comprises a list of elements is not necessarily limited to only those elements, but may include other elements not expressly listed or inherent to such process, method, article, or apparatus.

The singular forms "a", "an", and "the" include plural referents unless the context clearly dictates otherwise.

The cationic polymer concentration as used herein means that cationic polymer concentration in target water samples before addition of polymer dispersants solution and phosphate solutions.

Disclosed are improved methods of using turbidity to determine the concentration of cationic polymers in a target water sample. The detectable cationic polymers include, but are not limited to, a polymer of epichlorhydrin-dimethylamine crosslinked with either ammonia or ethylenediamine; a linear polymer of epichlorohydrindimethylamine; a homopolymer of polyethyleneimine; polydiallyldimethylammonium chloride and a polymer of (meth)acrylamide and one or more cationic monomer selected from the group consisting of: dimethylaminoethyl(meth)acrylate methyl chloridequaternary salt, dimethylaminoethyl(meth)acrylate methyl sulfate quaternary salt, dimethylaminoethyl(meth)acrylate benzyl chloride quaternary slat, dimethylaminoethyl (meth)acrylate sulfuric acid salt, dimethylaminoethyl(meth) acrylate hydrochloric acid salt, dialkylaminoalkylacrylamides or methacrylamides and their quaternary or acid slats, acrylamidopropyltrimethylammonium chloride, dimethylaminopropyl(meth)acrylamide methyl sulfate quaternary salt, and dimethylaminopropyl (meth)acrylamide hydrochloric acid salt, diethylaminoethylacrylate, diethylaminoethylmethacrylate, diallyldiethylammonium chloride, and diallyldimethyl ammonium chloride. The target water sample is a sample of water taken from an aqueous system including, but not limited to, a wastewater treatment system, a drinking water treatment system, a food process water treatment system and membrane process water treatment system.

Applicants have discovered that the concentration of cationic polymers in a target water sample can be measured by obtaining a target water sample containing a cationic polymer and adding a polymer dispersant solution containing calcium and a phosphate solution to the target water sample. In the presence of phosphate, calcium will precipitate and produce turbidity in water. The polymer dispersants inhibit precipitation of calcium phosphate and disperse calcium phosphate in small particles (<200 nm).

Once the polymer dispersant solution and phosphate solution are added to the target water sample, the target water sample is left to stand for a length of time. The target water sample is in a quasi stable state, such that it is very sensitive to low concentration of coagulants and flocculants, especially cationic polymers. After the target water sample is left to stand for a length of time, the turbidity of the target water sample is measured. To determine the concentration of cationic polymers in the target water sample, this turbidity measurement is compared with a calibration curve of the turbidity of samples containing known concentrations of cationic polymers.

In order to determine the concentration of cationic polymers in a target water sample, it is first necessary to generate a calibration curve for each cationic polymer. Further, if the turbidity response is dependent upon the pH, it is also necessary to generate a calibration curve for each cationic polymer of interest at the same pH level of the target water sample of interest. A pH buffer could also be added to target water sample to stabilize pH of target sample. Calibration curves are generated by preparing various target water samples containing known amounts of a cationic polymer, adding a polymer dispersant solution and a phosphate solution to the target water sample, standing the target water sample for a length of time, and measuring the turbidity of the target water sample. The calibration curve is then a plot of the turbidity vs. the known cationic polymer concentration. It is contemplated that in some embodiments, the sample stands for about 1-15 minutes. However, it is contemplated that in other embodiments, the sample stands for about 2-10 minutes. Further, it is contemplated that is additional embodiments; the sample stands for about 3-6 minutes.

Once created, the calibration curve can be used to determine the cationic polymer concentration of a target water sample by comparing the turbidity of the target water sample with the calibration curve and reading the cationic polymer concentration of the curve. In order to use the calibration curve, the turbidity meter used to measure the turbidity of a target water sample having an unknown cationic polymer concentration must be the same or operate on similar conditions as the device that was used to create the calibration curve. The turbidity may be measured using any suitable device known in the art to measure turbidity. In one embodiment, turbidity measurements can be performed using a Hach 2100P turbidmeter, which is available from Hach Company of Loveland, Colo.

In one embodiment, it is contemplated that the total hardness of the target water sample is controlled between about 200 ppm to about 15000 ppm after the addition of the polymer dispersant solution and the phosphate solution. However it is contemplated that total hardness of the target water sample is controlled between about 300 ppm to about 10000 ppm. Further, it is contemplated that total hardness is controlled between about 500 ppm to 7000 ppm. Additionally, it is contemplated that the phosphate in said phosphate solution is controlled between about 5 ppm to about 100 ppm after the addition of said polymer dispersant solution and said phosphate solution to said target water sample. However it is contemplated that the phosphate is controlled between about 8 ppm to about 80 ppm. Further it is contemplated that the phosphate is controlled between about 10 ppm to about 50 ppm. Accordingly, it is contemplated that bicarbonate/carbonate in phosphate solution is controlled between about 20 ppm to about 300 ppm after the addition of said polymer dispersant solution and said phosphate solution to said target water sample.

Further, it is contemplated that the polymer dispersant in said polymer dispersant solution is controlled between about 5 ppm to about 100 ppm after the addition of said polymer dispersant solution and said phosphate solution to said target water sample. However it is contemplated that the polymer dispersant is controlled between about 8 ppm to about 70 ppm. Further it is contemplated that the polymer dispersant is controlled between about 10 ppm to about 40 ppm.

The examples below demonstrate that the response correlation shows good linearity between turbidity and the cationic polymer concentration of a target water sample. Further, this linearity is maintained at low levels, such that it is able to detect low limit cationic polymer in the range of 0-1 ppm.

Polymer dispersants are widely used to inhibit calcium carbonate, calcium phosphate and other inorganic deposition, such as including acrylamido sulfonic acid polymers and copolymers such as 2-acrylamido-2-methyl propane sulfonic acid (AMPS) and acrylic acid/AMPS copolymers, acrylic acid homopolymers and copolymers, and anionic salts thereof, maleic anhydride homopolymers and copolymers such as sulfonated styrene maleic anhydride copolymers, acrylamide polymers and copolymers, vinyl pyrrolidone, vinyl amide polymers, maleic acid homopolymers and copolymers, itaconic acid homopolymers and copolymers, vinyl sulfonic acid polymers, styrene sulfonic acid polymers, vinyl phosphonic polymers, etc.

The phosphate solution contains phosphate and a calcium phosphate inhibition polymer. Exemplary polymer dispersants used in the polymer dispersant solutions discussed in the examples are selected from but not limited to acrylic acid/2-hydroxypropylacrylate copolymers, acrylic acid/1-allyloxy-2-hydroxypropylsulfonic acid copolymers, and acrylic acid/polyethyleneglycol monoallyl ether sulfate/1-allyloxy-2-hydroxypropylsulfonic acid terpolymer as described in U.S. Pat. No. 4,869,845, U.S. Pat. No. 6,441,754, and U.S. Pat. No. 6,444,747.

The present disclosure will now be described more specifically with reference to the following examples. It is to be noted that the following examples are presented herein for purpose of illustration and description; they are not intended to be exhaustive or to limit the disclosure to the precise form disclosed.

Example 1

This example demonstrates the interaction between polyDADMAC and terpolymer of acrylic acid/polyethyleneglycol monoallyl ether sulfate/1-allyloxy-2-hydroxypropylsulfonic acid in high range (>1 ppm) in effluent of the secondary clarifier of a GE China Technology Center (CTC) waste water treatment plant. In this example, the secondary clarifier effluent of CTC wastewater treatment plant was filtrated by 1.2-micron filter paper to create water samples. Different concentrations of polyDADMAC active in the range of 0-6 ppm were added to the water samples. 10 ppm terpolymer active was then added to the water samples.

The water samples were then filtered by 0.22-micron filter paper again, and the residual terpolymer of filtrate was detected with GE BETZ Polymer Dispersant Turbidity Test Kit (from GE Betz, Trevose, Pa.).

Figure 1:
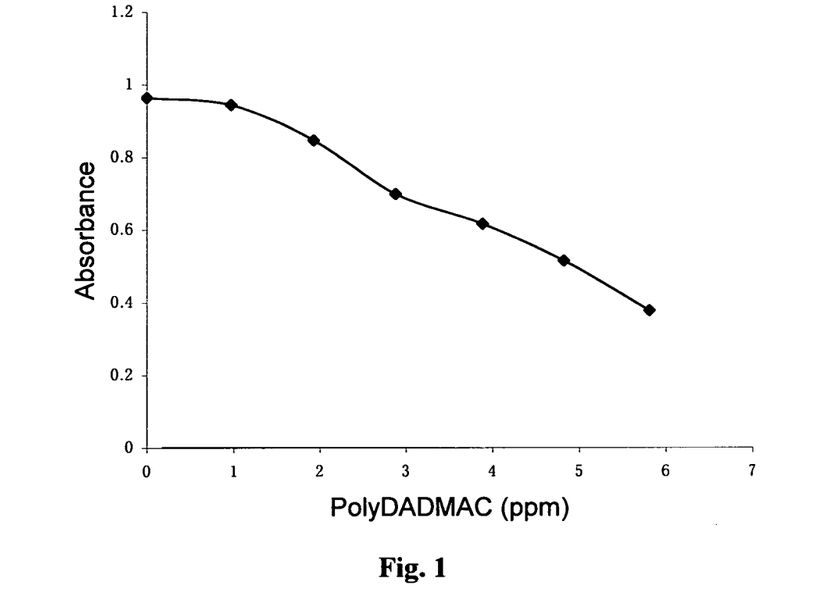
FIG. 1 depicts a plot of terpolymer dispersant absorbance vs. concentration for polyDADMAC in waste water.

The absorbance was then plotted as a function of polyDADMAC concentration in FIG. 1. Accordingly, it can be seen that there is a strong correlation between residual terpolymer dispersant absorbance and polyDADMAC concentration in the range of 1-6 ppm. However, there is not a strong enough correlation between residual polymer dispersant absorbance and polyDADMAC concentration in the range of 0-1.0 ppm. Accordingly, the residual polymer dispersant absorbance is not sensitive enough to accurately detect 0-1.0 ppm concentrations of polyDADMAC. This result indicates that typical turbidmetry of complexes between oppositely charged polymers does not work well for low level residual cationic polymers detection.

Example 2

This example demonstrates the use of the terpolymer used in Example 1 and $Ca_3(PO_4)_2$ to detect low limit polyDADMAC. In this example, different dosages of quantitative (0-0.4 ppm) polyDADMAC were added to deionized (DI) water to create water samples. 400 ppm Ca hardness as $CaCO_3$, 100 ppm Mg as $CaCO_3$, 35 ppm M-Alk as $CaCO_3$, and 10 ppm terpolymer, and 11.5 ppm $PO_4$ were also added to the water samples.

Figure 2:
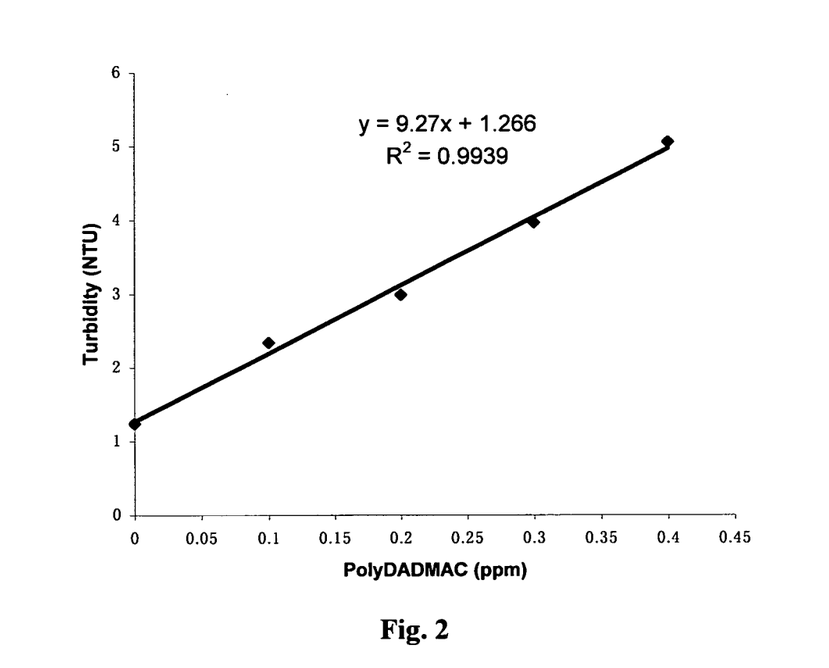
FIG. 2 depicts a plot of turbidity vs. concentration for polyDADMAC in DI water with terpolymer dispersant, total hardness and phosphate.

The water samples were then allowed to rest for about 5 minutes and the turbidity of the target water samples were then recorded for the various concentrations of polyDADMAC. The turbidity was then plotted as a function of polyDADMAC concentration in FIG. 2. Accordingly, it can be seen that there is a strong linear relationship between turbidity and polyDADMAC in the concentration range of 0-0.4 ppm.

Example 3

This example demonstrates the use of copolymer dispersant of acrylic acid and 1-allyoxy-2-hydroxypropylsulfonic acid and $Ca_3(PO_4)_2$ to detect low limit polyDADMAC. In this example, a polymer dispersant solution, a phosphate solution, and target water samples were prepared. The polymer dispersant solution contained 400 ppm copolymer, 70.56 g/L $CaCl_2.2H_2O$ and 32.4 g/L $MgCl_2.6H_2O$. The phosphate solution contained 1 g/L $NaHCO_3$ and 317 ppm phosphate. The target water samples were prepared using different dosages of polyDADMAC (0-0.85 ppm) in DI water.

Figure 3:
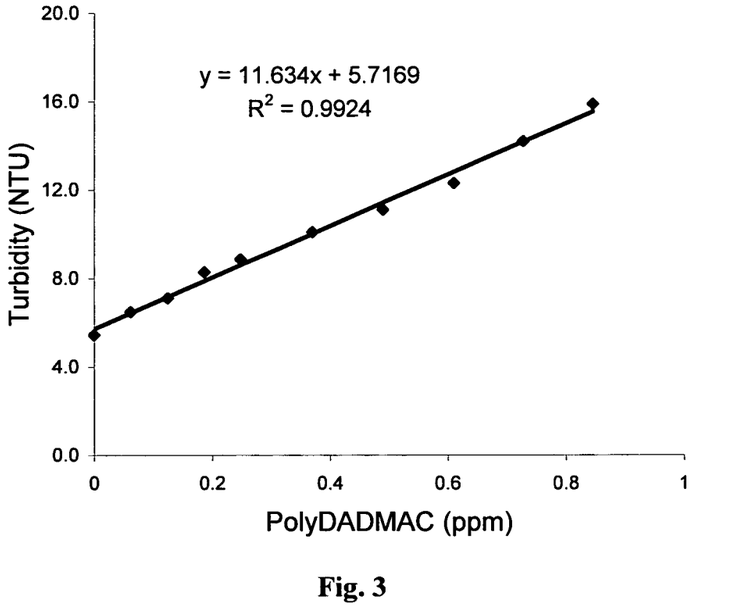
FIG. 3 depicts a plot of turbidity vs. concentration for polyDADMAC; in DI water with copolymer dispersant, total hardness and phosphate.

1.5 ml of the polymer dispersant solution was added to 12.0 ml of the target water samples, and the samples were then well mixed. 1.5 ml of the phosphate solution was then added sequentially and well mixed. The target water samples were allowed to rest for 6 minutes and the turbidity of the target water samples were then recorded for the various concentrations of polyDADMAC. The turbidity was then plotted as a function of polyDADMAC concentration in FIG. 3. Accordingly, it can be seen that there is a strong linear relationship between turbidity and polyDADMAC in the concentration range of 0-0.85 ppm.

Example 4

This example demonstrates the use of the copolymer dispersant as described in Example 3 and $Ca_3(PO_4)_2$ to detect low limit polyDADMAC in wastewater. In this example, a polymer dispersant solution, a phosphate solution, and target water samples were prepared. The polymer dispersant solution contained 400 ppm copolymer dispersant, 70.56 g/L $CaCl_2.2H_2O$ and 32.4 g/L $MgCl_2.6H_2O$. The phosphate solution contained 2 g/L $NaHCO_3$ and 320 ppm $PO_4$. The target water samples were prepared by taking the secondary clarifier effluent of the CTC wastewater treatment plant, filtering the effluent with 1.2-micron filter paper, and mixing the effluent with different dosages of polyDADMAC (0-0.81 ppm). The specification of the waste water filtrate is listed in Table 1.

TABLE 1

| | | | | Specification of CTC $2^{nd}$ clarifier effluent wastewater | | | | | |
|---|---|---|---|---|---|---|---|---|---|
| Turbidity (NTU) | Conductivity μS/cm | pH | Phosphate (ppm) | Caclium Hardness (ppm) | Total Hardness (ppm) | N—$NH_3$ (ppm) | Total-N (ppm) | TDS (ppm) | COD (ppm) |
| 0.28 | 1234 | 7.2 | 17 | 156 | 186 | 18 | 78 | 628 | 117 |

Figure 4:
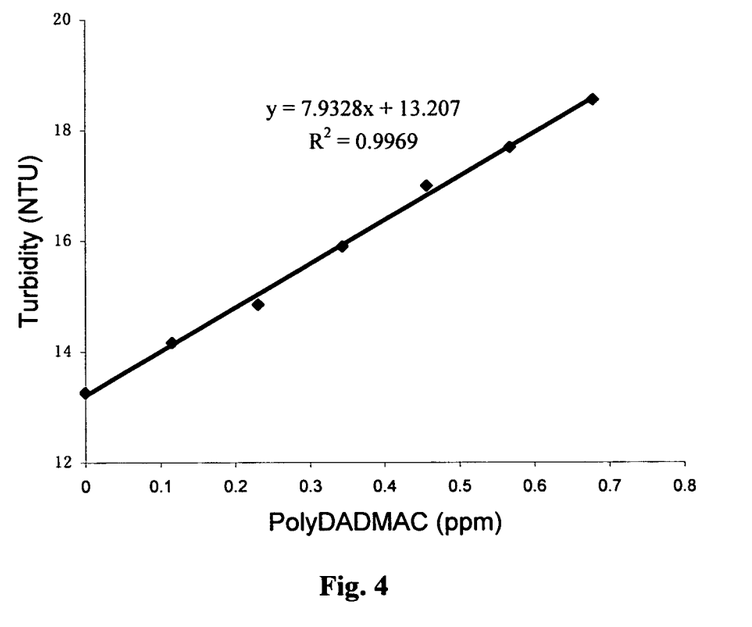
FIG. 4 depicts a plot of turbidity vs. concentration for polyDADMAC in wastewater with copolymer dispersant, total hardness and phosphate.

1.5 ml of the polymer dispersant solution was added to 11.5 ml of each of the target water sample, and the samples were then well mixed. 2.0 ml of the phosphate solution was then added sequentially and well mixed. The target water samples were allowed to rest for 3 minutes and the turbidity of the target water samples were then recorded for the various concentrations of polyDADMAC. The turbidity was then plotted as a function of polyDADMAC concentration in FIG. 4. Accordingly, it can be seen that there is a strong linear relationship between turbidity and polyDADMAC in the concentration range of 0-0.68 ppm.

Example 5

Figure 5:
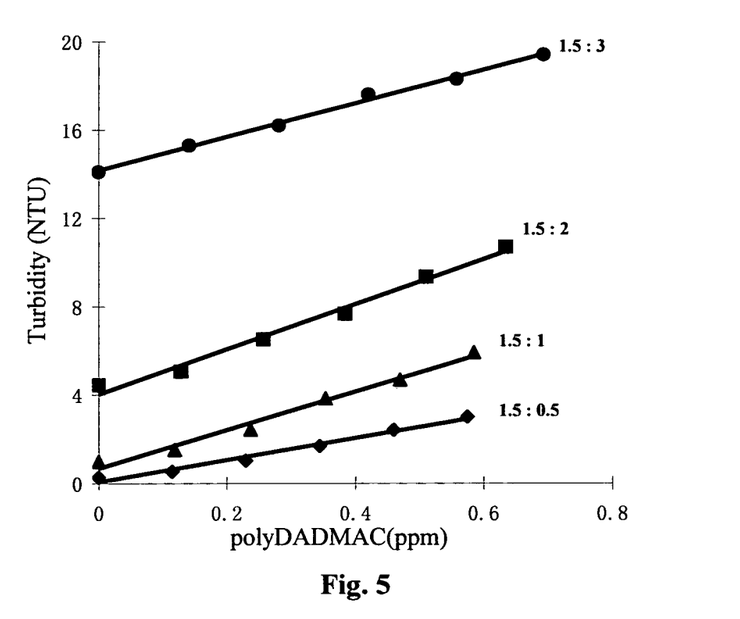
FIG. 5 depicts a series plots of turbidity vs concentration for polyDADMAC with different ratio between polymer solution and phosphate solution in DI water.

In this example, polymer dispersant solution and phosphate solution used are the same as described in Example 3. 1.5 ml of the polymer dispersant solution was added to each target DI water sample, and the samples were then well mixed. Different volumes of phosphate solution were then added sequentially and well mixed. The total volume of polymer dispersant solution, phosphate solution and target water samples was 15 ml. The formulations and results were listed in Table 2. The target water samples were allowed to rest for 3 minutes and the turbidity of the target water samples were then recorded for the various concentrations of polyDADMAC. The turbidity was then plotted as a function of polyDADMAC concentration in FIG. 5. Accordingly, it can be seen that there are good linear relationships between turbidity and polyDADMAC as the final phosphate concentration in the range of 10-65 ppm and final $NaHCO_3$ concentration in the range of 30-200 ppm.

TABLE 2

| Formulation and testing results | | | | |
|---|---|---|---|---|
| | 1.5:0.5 | 1.5:1 | 1.5:2 | 1.5:3 |
| Target water (ml) | 13.0 | 12.5 | 11.5 | 10.5 |
| Polymer solution (ml) | 1.5 | 1.5 | 1.5 | 1.5 |
| Phosphate solution (ml) | 0.5 | 1.0 | 2.0 | 3.0 |
| Phosphate (ppm) | 10.6 | 21.1 | 42.3 | 63.4 |
| $NaHCO_3$(ppm) | 33 | 67 | 133 | 200 |
| Slope | 5.0 | 8.7 | 10.2 | 7.6 |
| Interception | 0.1 | 0.7 | 4.0 | 14.2 |
| R-square | 0.9822 | 0.9852 | 0.9864 | 0.9955 |

Example 6

Figure 6:
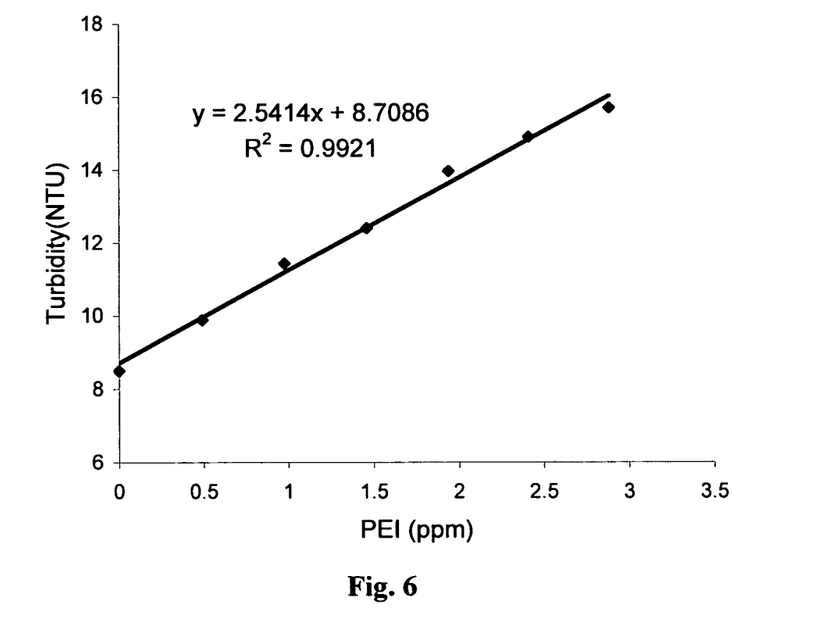
FIG. 6 depicts a plot of turbidity vs concentration for polyethyleneimine in DI water with copolymer dispersant, total hardness and phosphate.
Figure 7:
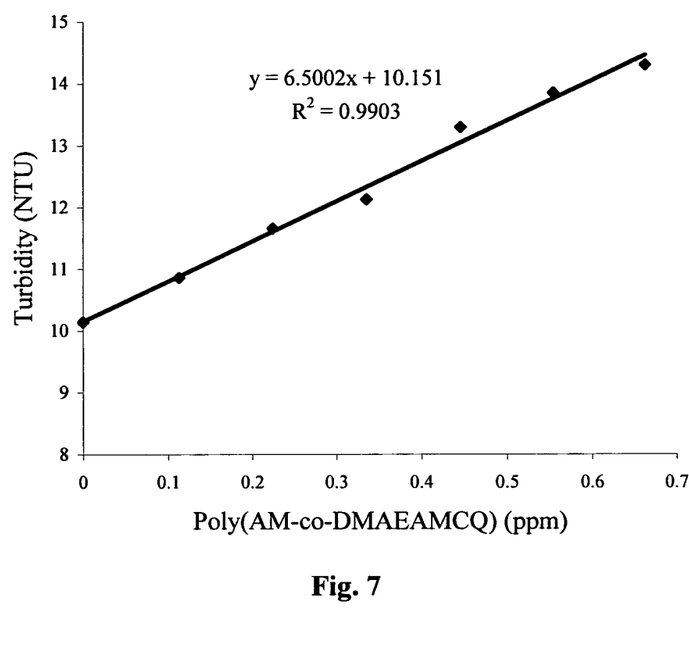
FIG. 7 depicts a plot of turbidity vs concentration for copolymer of acrylamide and dimethylaminoethylacrylate methyl chloride quaternary salt in waste water with copolymer dispersant, total hardness and phosphate.

This example demonstrates the use of the same polymer dispersant solution, phosphate solution and related volume ratio as described in Example 4 to detect copolymer of acrylamide(AM)/dimethylaminoethylacrylate methyl chloride quaternary salt (DMAEAMCQ) (55 mol % AM-co-45 mol % DMAEAMCQ) and polyethyleneimine(PEI). The turbidity was then plotted as functions of Poly (AM-co-DMAE-AMCQ) in FIG. 6 in wastewater treatment system effluent as described in Table 1. The turbidity was also plotted as a function of PEI in FIG. 7 in DI water systems. Accordingly, it can be seen that there is a strong linear relationship between turbidity and PEI in the concentration range of 0-3.0 ppm in FIG. 6. In FIG. 7, it also can be seen that there is a good linear relationship between tubidity and poly (AM-co-DMAE-AMCQ) in range of 0-0.7 ppm.

Example 7

In this sample, 39 ppm copolymer dispersant stock solution was prepared in DI water and the copolymer is the same as described in Example 3. 26.7 ppm PolyDADMAC stock solution was also prepared. A series volumes of polyDADMAC stock solution was then added sequentially to each 11.5 ml copolymer dispersant solution and well mixed. The solutions were then allowed to rest for 3 minutes and the turbidity results were listed in Table 3

TABLE 3

| Turbidity with different polyDADMAC dosage in 39 ppm copolymer solution | | | | | | |
|---|---|---|---|---|---|---|
| | PolyDADMAC Stock (μl) | | | | | |
| | 0 | 50 | 100 | 200 | 300 | 400 |
| PolyDADMAC Dosage (ppm) | 0 | 0.12 | 0.23 | 0.46 | 0.68 | 0.90 |
| Turbidity (NTU) | 1.47 | 1.60 | 1.24 | 1.34 | 1.26 | 1.46 |

It can be seen that there is no any relationship between turbidity and polyDADMAC concentration without total hardness and phosphate. Typical complexes between oppositely charged polymers do not contribute any turbidity in above testing systems.

While this invention has been described in conjunction with the specific embodiments described above, it is evident that many alternatives, combinations, modifications and variations are apparent to those skilled in the art. Accordingly, the preferred embodiments of this invention, as set forth above are intended to be illustrative only, and not in a limiting sense. Various changes can be made without departing from the spirit and scope of this invention. Therefore, the technical scope of the present invention encompasses not only those embodiments described above, but also all that fall within the scope of the appended claims.

This written description uses examples to disclose the invention, including the best mode, and also to enable any person skilled in the art to practice the invention, including making and using any devices or systems and performing any incorporated processes. The patentable scope of the invention is defined by the claims, and may include other examples that occur to those skilled in the art. These other examples are intended to be within the scope of the claims if they have structural elements that do not differ from the literal language of the claims, or if they include equivalent structural elements with insubstantial differences from the literal language of the claims.

What is claimed is:

1. A method of determining a concentration of residual cationic polymers present at less than 1 ppm in a target water sample, said method comprising:
adding a polymer dispersant solution and a phosphate solution to said target water sample, wherein:
said polymer dispersant solution comprises calcium hardness and at least one calcium phosphate inhibition polymer dispersant therein and wherein said polymer dispersant is selected from the group consisting of acrylic acid/2-hydroxypropylacrylate copolymers, acrylic acid/1-allyloxy-2-hydroxypropylsulfonic acid copolymers, acrylic acid/polyethyleneglycol monoallyl ether sulfate/1-allyoxy-2-hydroxypropylsulfonic acid terpolymers, and combinations thereof;
and wherein said phosphate solution comprises at least one phosphate therein;
standing said target water sample for about 1-15 minutes to allow the formation of calcium phosphate;
measuring a turbidity of said target water sample produced by said calcium phosphate; and
comparing said turbidity of said target water sample with a turbidity calibration curve of samples containing known concentrations of cationic polymers to determine a concentration of said residual cationic polymers in said target water sample.

2. The method of claim 1, wherein the phosphate in said phosphate solution is controlled between about 5 ppm to about 100 ppm after the addition of said polymer dispersant solution and said phosphate solution to said target water sample.

3. The method of claim 1, wherein the phosphate in said phosphate solution is controlled between about 8 ppm to about 80 ppm after the addition of said polymer dispersant solution and said phosphate solution to said target water sample.

4. The method of claim 1, wherein the phosphate in said phosphate solution is controlled between about 10 ppm to about 50 ppm after the addition of said polymer dispersant solution and said phosphate solution to said target water sample.

5. The method of claim 1, wherein any bicarbonate or carbonate in said phosphate solution is controlled between about 20 ppm to about 300 ppm.

6. The method of claim 1, wherein said cationic polymer is a polymer of (meth)acrylamide and one or more cationic monomer selected from the group consisting of: dimethylaminoethyl(meth)acrylate methyl chloride quaternary salt, dimethylaminoethyl(meth)acrylate methyl sulfate quaternary salt, dimethylaminoethyl(meth)acrylate benzyl chloride quaternary salt, dimethylaminoethyl(meth)acrylate sulfuric acid salt, dimethylaminoethyl(meth)acrylate hydrochloric acid salt, dialkylaminoalkylacrylamides or methacrylamides and their quaternary or acid salts, acrylamidopropyltrimethylammonium chloride, dimethylaminopropyl(meth)acrylamide methyl sulfate quaternary salt, and dimemylaminopropyl(meth)acrylamide hydrochloric-acid-salt, -diemylaminoethylacrylate, diemylaminoethylmethacrylate, diallyldiethylammonium chloride, and diallyldimethyl ammonium chloride.

7. The method of claim 1, wherein said cationic polymer is selected from a polymer of epichlorohydrin-dimethylamine crosslinked with either ammonia or ethylenediamine; a linear polymer of epichlorohydrindimethylamine; a homopolymer of polyethyleneimine; polydiallyldimethylammonium chloride.

8. The method of claim 1, wherein said cationic polymer is polydiallyldimethylammonium chloride.

9. The method of claim 1, wherein said cationic polymer is copolymer of acrylamide and dimethylaminoethylacrylate methyl chloride quaternary salt.

10. The method of claim 1, wherein said cationic polymer is polyethyleneimine.

11. The method of claim 1, wherein said polymer dispersant solution further comprises magnesium hardness.

12. The method of claim 11, wherein the total hardness of said target water sample is controlled between about 200 ppm to about 15000 ppm after the addition of said polymer dispersant solution and said phosphate solution.

13. The method of claim 11, wherein the total hardness of said target water sample is controlled between about 300 ppm to about 10000 ppm after the addition of said polymer dispersant solution and said phosphate solution.

14. The method of claim 11, wherein the total hardness of said target water sample is controlled between about 500 ppm to about 7000 ppm after the addition of said polymer dispersant solution and said phosphate solution.

15. The method of claim 11, wherein the polymer dispersant in said polymer dispersant solution is controlled between about 5 ppm to about 100 ppm after the addition of said polymer dispersant solution and said phosphate solution to said target water sample.

16. The method of claim 11, wherein the polymer dispersant in said polymer dispersant solution is controlled between about 8 ppm to about 70 ppm after the addition of said polymer dispersant solution and said phosphate solution to said target water sample.

17. The method of claim 11, wherein the polymer dispersant in said polymer dispersant solution is controlled between about 10 ppm to about 40 ppm after the addition of said polymer dispersant solution and said phosphate solution to said target water sample.

18. The method of claim 1, wherein said method further comprises filtrating said target water sample to remove any suspended solids therein before adding said polymer dispersant solution and said phosphate solution to said target water sample.

19. The method of claim 18, wherein said filtrating step uses less than 1.2 micron pore size filter paper.

20. The method of claim 18, wherein said filtrating step uses less than 5 micron pore size filter paper.

21. The method of claim 1, wherein said target water sample is allowed to stand for about 2-10 minutes.

22. The method of claim 21, wherein said target water sample is allowed to stand for about 3-6 minutes.

* * * * *